United States Patent [19]

Suchy

[11] 4,200,587
[45] Apr. 29, 1980

[54] 2-[P-(P-SUBSTITUTED PHENOXY)PHENOXY]PROPIONYL OXIMES

[75] Inventor: Milos Suchy, Pfaffhausen, Switzerland

[73] Assignee: Hoffmann-La Roche Inc., Nutley, N.J.

[21] Appl. No.: 962,087

[22] Filed: Nov. 20, 1978

[30] Foreign Application Priority Data

Nov. 28, 1977 [LU] Luxembourg .......................... 78591
Sep. 15, 1978 [CH] Switzerland ........................ 9667/78

[51] Int. Cl.$^2$ ................. C07C 131/00; C07C 131/02; C07C 131/04
[52] U.S. Cl. .............................. 260/566 AE; 71/113; 560/61; 560/62; 562/471; 562/472; 71/113
[58] Field of Search ................................ 260/566 AE

[56] References Cited

U.S. PATENT DOCUMENTS

| 3,592,920 | 7/1971 | Gutman et al. | 260/566 AE |
| 3,644,524 | 2/1972 | Cahoy | 260/566 AE |
| 3,925,473 | 12/1975 | Nüsslein et al. | 260/566 AE |
| 4,059,625 | 11/1977 | Baker et al. | 260/566 AE |
| 4,079,149 | 3/1978 | Henry | 260/566 AE |

FOREIGN PATENT DOCUMENTS

7317222  6/1974  Netherlands ................... 260/566 AE

*Primary Examiner*—Paul J. Killos
*Attorney, Agent, or Firm*—Jon S. Saxe; Bernard S. Leon; William M. Farley

[57] ABSTRACT

2-[p-(p-substituted phenoxy)phenoxy] propionyl oximes, processes for their preparation, herbicidal compositions containing these oximes and methods of use of the herbicidal compositions are disclosed.

20 Claims, No Drawings

2-[P-(P-SUBSTITUTED PHENOXY)PHENOXY]PROPIONYL OXIMES

BACKGROUND OF THE INVENTION

In German DOS No. 2,223,894 and DOS No. 2,531,643, 2-[p-(p-substitutedphenoxy)phenoxy] propionic acid esters of the general formula

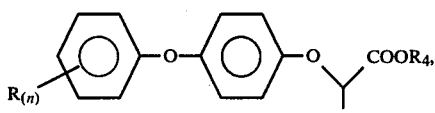

wherein $R_4$ is hydroxy, alkoxy, thioalkyl, alkenyloxy cyclohexyloxy and the like, R is hydrogen, halogen alkyl, alkoxy, alkylthio, cyclohexyl, cyclopentyl, phenyl, trifluoromethyl and the like and n is an integer from 1 to 3 are disclosed as herbicides. Compounds similar to the general formula above are also disclosed in U.S. Pat. No. 3,646,200 and German DOS Nos. 2,136,828; 2,601,548 and 2,358,789 and DAS No. 1,668,896. Further, in German DOS No. 2,262,402 compounds of the general formula

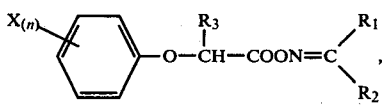

wherein $R_1$ and $R_2$ are aromatic, having one or more substituents, aliphatic, cycloaliphatic, araliphatic or heterocyclic hydrocarbon groups; $R_1$ can also be hydrogen; $R_1$ and $R_2$ together can be nitrogen or oxygen-containing cycloaliphatic hydrocarbon groups; $R_3$ is hydrogen or alkyl, X is hydrogen, alkyl, alkoxy, haloalkyl or halogen, and n is an integer from 1 to 3, are disclosed as herbicides.

SUMMARY OF THE INVENTION

This invention is directed to compounds of the formula

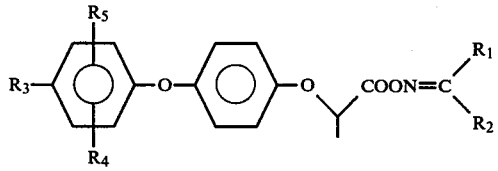

wherein $R_1$ is hydrogen, alkyl of from 1 to 6 carbon atoms or phenyl; $R_2$ is hydrogen, alkyl of from 1 to 6 carbon atoms, alkenyl of from 2 to 6 carbon atoms, alkynyl of from 2 to 6 carbon atoms or phenyl; or $R_1$ and $R_2$ together are cyclohexane which can, optionally, be mono-substituted, disubstituted or trisubstituted with alkyl of from 1 to 3 carbon atoms, $R_3$ is hydrogen, fluorine, chlorine, bromine, trifluoromethyl or nitro and $R_4$ and $R_5$ represent hydrogen or chlorine, with the proviso that $R_1$ and $R_2$ are not both hydrogen, as well as processess for their preparation. This invention is also directed to herbicidal compositions containing, as the active ingredient, a compound of formula I and methods for the use of these herbicidal compositions.

DETAILED DESCRIPTION OF THE INVENTION

The invention is directed to compounds of the formula

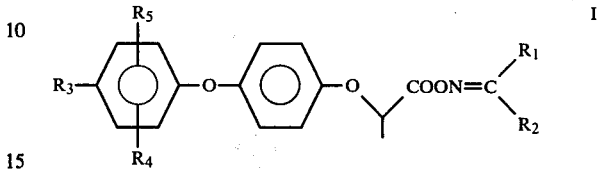

wherein $R_1$ is hydrogen, alkyl of from 1 to 6 carbon or phenyl; $R_2$ is hydrogen, alkyl of from 1 to 6 carbon, alkenyl of from 2 to 6 carbon, alkynyl of from 2 to 6 carbon or phenyl; or $R_1$ or $R_2$, together are cyclohexane which can be optionally, monosubstituted, disubstituted or trisubstituted with alkyl of from 1 to 3 carbon atoms, $R_3$ is hydrogen, fluorine, chlorine, bromine, trifluoromethyl or nitro and $R_4$ and $R_5$ are hydrogen or chlorine, with the proviso that $R_1$ and $R_2$ are not both hydrogen.

This invention is also directed to processes for the preparation of the compounds of formula I as well as herbicidal compositions, and methods for their use, which contain, as the active ingredient, a compound of formula I. The compounds have both pre-emergence and post-emergence herbicidal activity.

The term alkyl encompasses both straight- and branched-chain hydrocarbon groups containing from 1 to 3 or 1 to 6 carbon atoms such as methyl, ethyl, propyl, isopropyl, butyl, isobutyl and t-butyl.

The terms alkenyl and alkynyl encompass both straight- and branched-chain unsaturated hydrocarbon groups such as allyl, butenyl, isobutenyl, pentenyl, isopentyl and the like and propargyl, butynyl, isobutynyl, pentynyl and the like.

Preferred compounds of formula I are those wherein $R_1$ and $R_2$ are methyl, ethyl or phenyl; $R_3$ is chlorine or trifluoromethyl and $R_4$ and $R_5$ are hydrogen.

Particularly preferred compounds are

Acetone O-[2-[p-(p-chlorophenoxy)-phenoxy]propionyl]-oxime,

2-Butanone O-[2-[p-(p-chlorophenoxy)phenoxy]propionyl]-oxime,

Benzaldehyde O-[2-[p-(p-chlorophenoxy)phenoxy]propionyl]-oxime, 2-(6-Methyl-5-heptenone) O-[2-[p-(p-chlorophenoxy)-phenoxy]propionyl]-oxime, 6-Undecanone O-[2-[p-(p-chlorophenoxy)phenoxy]propionyl]oxime, Cyclohexanone O-[2-[p-(p-chlorophenoxy)phenoxy]-propionyl]-oxime, Acetone O-D-[2-[p-(p-chlorophenoxy)phenoxy]propionyl]-oxime, 2-(3-Butynone) O-[2-[p-(p-chlorophenoxy)phenoxy]propionyl]-oxime, Acetone O-[2-[p-(p-trifluoromethylphenoxy)phenoxy]-propionyl]-oxime, Acetophenone O-[2-[p-(p-trifluoromethylphenoxy)-phenoxy]propionyl]-oxime, 2-Butanone O-[2-[p-(p-trifluoromethylphenoxy)-phenoxy]propionyl]-oxime, 6-Undecanone O-[2-[p-(p-trifluoromethylphenoxy)-phenoxy]propionyl]-oxime, Benzaldehyde O-[2-[p-(trifluoromethylphenoxy)-phenoxy]propionyl]-oxime,
Acetone O-D-[2-[p-(p-trifluoromethylphenoxy)phenoxy]propionyl]-oxime,
Acetone O-[2-[p-(2,4-dichlorophenoxy)phenoxy]propionyl]-oxime,
Acetone O-[2-[p-(p-bromophenoxy)phenoxy]propionyl]-oxime,
Acetone O-[2-[p-(3,4-dichlorophenoxy)phenoxy]propionyl]-oxime and
Acetone O-[2-[p-(2,6-dichlorophenoxy)phenoxy]propionyl]-oxime.

The compounds of formula I are prepared by one of the procedures described below:

A. The esterification of a reactive derivative of an acid of the formula

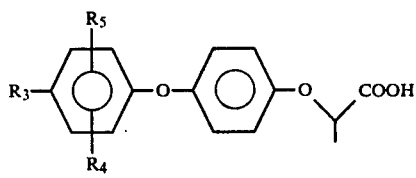  II with an oxime of the formula $R_1R_2CNOH$  III $R_1$, $R_2$, $R_3$, $R_4$ and $R_5$ have the same significance as in formula I above. The expression "reactive derivative of an acid" refers to an acid halide or an acid anhydride.

The esterification is preferably carried out in a suitable inert solvent either at room temperature or at an elevated temperature. The preferred temperature range is $-10°$ to $100°$ C. with $20°$ to $70°$ C. especially preferred.

If an acid halide is the reactive derivative, the reaction with the oxime is carried out at room temperature in the presence of an acid acceptor, e.g. a tertiary amine such as pyridine or triethylamine, or in an alkaline solution as in the Schotten-Bauman reaction. Preferred acid halides are the acid chlorides. The corresponding ester is obtained in high yield. Suitable inert solvents include benzene, toluene or petroleum ether and, in the case of the Schotten-Bauman reaction, an alkaline solution.

If an acid anhydride is the reactive derivative, the reaction with the oxime is carried out by heating the anhydride with the oxime in the presence of a base, preferably an alkali metal carbonate. Especially preferred is sodium carbonate. The corresponding alkanecarboxylic acid ester is obtained in high yield.

B. The reaction of an oxime of the formula

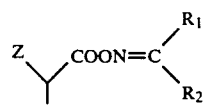  IV with an alcohol of the formula

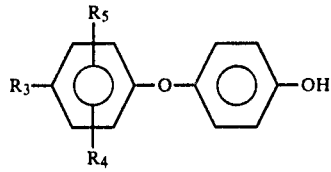  V or an alkali metal salt thereof in the presence of a base.

$R_1$, $R_2$, $R_3$, $R_4$ and $R_5$ have the same significance as in formula I above and Z is chlorine, bromine, iodine, mesyloxy or tosyloxy.

An oxime of formula IV is reacted with an alkali metal salt of the alcohol of formula V by known procedures. The reaction is carried out in an inert organic hydrocarbon solvent such as benzene, toluene, ethers, e.g. diethyl ether, tetraydrofuran or dimethoxyethane or hexamethylphosphonic triamide. Temperature and pressure are not critical. The reaction is carried out at a temperature of from about $-20°$ C. to the reflux temperature of the reaction mixture, preferably between $-10°$ and $30°$ C.

C. The esterification of an acid of formula II with an oxime of formula III in the presence of dicyclohexyl-carbodiimide.

In this reaction, the acid of formula II is dissolved in an inert organic solvent such as chlorinated hydrocarbons, e.g. methylene chloride, chloroform, carbon tetrachloride or trichloroethane; ethers, e.g. dicthyl ether, dissopropyl ether or dioxane and aromatic hydrocarbons, e.g. benzene, toluene, xylene or the like. The oxime of formula III is this suspended in this mixture.

Dicyclohexyl-carbodiimide is dissolved in the same solvent as used for the acid of formula II and this solution is then added to the reaction mixture.

The reaction can be carried out over a temperature range of from about $0°$ C. to the boiling temperature of the reaction mixture with the preferred temperature range being from room temperature to about $50°$ C.

After about 2 hours the reaction is complete. The reaction mixture is then filtered. The filtrate is evaporated and the residue is purified by, e.g. recrystallization or chromatography.

Since the substituted phenoxyalkanecarboxylic acid oxime ester of formula I have an asymmetric carbon atoms in the $\alpha$-position, these compounds can exist in optically active isomeric forms. In fact, these esters can have more than one asymmetric carbon atoms. The racemic compounds can be resolved in their dextrorotatory and laevorotatory isomers using known procedures as, for example, that described in Industrial and Engineering Chemistry 60(8), 12–28, (1968). The racemic mixtures as well as the isomers all have herbicidal activity with the D-isomer having the highest activity followed by the racemic mixture and the L-isomer. For example, it has been found that the D-isomer of acetone O-[2-[p-(p-chlorophenoxy)phenoxy]-propionyl]oxime has a higher activity than the racemic mixture.

The isomers, and especially the D-isomer, can be prepared by synthesis from the corresponding optically active starting materials.

Examples of such optically active starting materials are optically active compounds of the D-form having the general formula

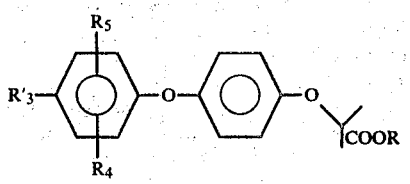

wherein R is hydrogen or alkyl of from 1 to 6 carbons, R'₃ is hydrogen, fluorine, bromine, trifluoromethyl or nitro and R₄ and R₅ are hydrogen or chlorine, with the proviso that R is alkyl of from 1 to 6 carbons when R'₃ is trifluoromethyl.

Starting materials which are particularly preferred include:
D-2-[p-(p-Bromophenoxy)phenoxy]-propionic acid,
D-2-[p-(p-Fluorophenoxy)phenoxy]-propionic acid,
D-2-[D-(p-Bromophenoxy)phenoxy]-propionic acid ethyl ester,
D-2-[p-(p-Nitrophenoxy)phenoxy]-propionic acid,
D-2-[p-(p-Trifluoromethylphenoxy)phenoxy]-propionic acid ethyl ester,
D-2-[p-(p-Trifluoromethylphenoxy)phenoxy]-propionic acid methyl ester.

The above optically active starting materials are also useful as herbicides since they have a spectrum of activity similar to the compounds of formula I. Compared to the particular racemate, these compounds have a lower phytotoxicity to, e.g. cotton and soy beans.

In addition, and as a result of the nitrogen-carbon double bond in the oxime group

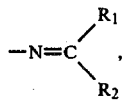

it is also possible to have two geometric isomers when $R_1$ and $R_2$ are different. These isomers, the syn- and anti-form, can also be isolated.

This invention is also directed to herbicidal compositions which comprise inert carrier material and, as the active ingredient, one or more compounds of formula I. These herbicidal compositions contain, as the inert carrier material, at least one of the following ingredients; carrier material, wetting agents, inert diluents and solvents.

The compounds of formula I are, in general, water-insoluble. Thus, the usual methods of formulation of insoluble material can be followed. For example, the compounds can be dissolved in a water-immiscible solvent such as a high-boiling hydrocarbon which contains dissolved emulsifiers. The solution acts as a self-emulsifiable oil when added to water.

The compounds of formula I can also be mixed with a wetting agent, with or without an inert diluent, to form a wettable powder which is soluble or dispersible in water. The compounds can be mixed with an inert diluent to form a solid or pulverulent powder.

Suitable inert diluents are solid inert media including pulverulent or finely divided solids such as clays, sand, talc, mica, fertilizers and the like. The resulting compositions can be either dusts or materials of relatively large particle size.

Wetting agents, suitable for use with the compounds of this invention, can be anionic, cationic or non-ionic.

Examples of anionic wetting agents include soaps, fatty sulfate esters, dodecyl sodium sulfate, octadecyl sodium sulfate and cetyl sodium sulfate; fatty aromatic sulfonates such as alkylbenzene-sulfonates and butyl-naphthalene-sulfonates and the more complex fatty sulfonates such as the amide condensation products of oleic acid and N-methyltaurine or the sodium sulfonate of dioctyl succinate.

Examples of cationic wetting agents include cetyl-trimethylammonium bromide and the like.

Examples of non-ionic wetting agents include, for example, condensation products of fatty acids, fatty alcohols or fatty-substituted phenols with ethyleneoxides; fatty acid esters and ethers of sugars of polyhydric alcohols, condensation products of these fatty acid esters and ethers of sugars of polyhydric alcohols with ethylene oxide and block copolymers of ethylene oxide and propylene oxide.

The herbicidal compositions of this invention can also be used in aerosol form using, in addition to the propellant gas, carrier material comprising a co-solvent and a wetting agent. Suitable propellant gases include the polyhalogenated alkanes such as dichlorodifluoromethane.

The herbicidal compositions of this invention can also contain other active ingredients such as synergistic agents, insecticidal bactericides, other herbicides and fungicides.

The compounds of this invention are useful as both pre-emergent and post-emergent herbicides. They are particularly suitable in combatting weeds such as slender foxtail (Alopecurus myosuroides) and millet varieties, such as prickly grass (Echinochloa crusgalli), giant foxtail (Setaria faberii) and witchgrass (Panicum capillare), in cereals. They are suitable for use against these weeds especially in cereals such as barley, oats and wheat and in rice, cotton, soya, sugar beet and vegetable crops.

The pre-emergent and post-emergent herbicidal compositions of this invention are especially preferred for combatting weeds in sugar-beet crops. For example, either acetone O-[2-[p-(p-chlorophenoxy)phenoxy]propionyl]oxime, 2-butanone O-[2-[p-(p-chlorophenoxy)-phenoxy]propionyl]-oxime or acetone O-[2-[p-(p-trifluoromethylphenoxy) phenoxy]propionyl]-oxime, applied at a concentration of 1.25 kg/ha, is sufficiently active against weeds without damaging the sugar beet crop.

In general, the compounds of this invention are effective as herbicides when applied at a concentration of from about 0.1 to about 6 kg/ha with the preferred concentration range being from about 0.6 to about 2.0 kg/ha. An especially preferred application rate is from about 1 to about 1.5 kg/ha.

The utility in cereal crops of compounds of formula I wherein $R_3$ is trifluoromethyl is limited since these compounds are somewhat phytotoxic. However, these compounds are particularly suitable for combatting weeds in rice, cotton, soya, sugar beet and vegetable crops.

The herbicidal compositions of this invention can be in the form of concentrates suitable for storage or shipment. Such compositions can contain, e.g. from about 2% to about 90% by weight, based on the weight of the total composition, of one or more of the active compounds of this invention. These concentrates can be diluted, with the same or different inert carrier material, to concentrations which are suitable for actual use. Ready-to-use compositions can contain concentrations of from 2% to 80% by weight of the active ingredient.

Particularly preferred concentrations of active ingredients in the herbicidal compositions of this invention are from about 2% to about 8% by weight and from about 50% to about 80% by weight The following Examples illustrate the invention:

EXAMPLE 1

1.1 g of a 50% suspension of sodium hydride in mineral oil are washed twice with 5.0 ml portions of tetrahydrofuran, under an inert gas atmosphere, and then added to 15.0 ml of tetrahydrofuran. A solution of 5.0 g of p-(p-chlorophenoxy)phenol in 30.0 ml of dimethylformamide, is, added dropwise to the mixture. 5.2 g of 2-bromopropionylacetone oxime in 20.0 ml of dimethylformamide are then added dropwise to the mixture. The reaction mixture is refluxed for 2 hours, cooled, poured onto ice and extracted exhaustively with ether. The ether extract is washed with water, dried over sodium sulphate and evaporated under reduced pressure, The product, acetone O-[2-[p-(p-chlorophenoxy)phenoxy]-propionyl]-oxime, is purified by adsorption onto silica gel; $n_D^{20}$: 1.5583.

The starting material, 2-bromopropionylacetone oxime, is prepared by dissolving 5.0 g of acetone oxime and 5.6 g of pyridine in 50 ml of tetrahydrofuran. 15.0 g of 2-bromopropionic acid bromide are added dropwise to this solution at 0° C. The mixture is then stirred at room temperature for 3 hours, poured onto ice and extracted with ether. The ether extract is washed with water, dried over sodium sulphate and evaporated under reduced pressure. The product, 2-bromopropionylacetone oxime is purified by adsorption onto silica gel, $n_D^{20}$: 1.4829.

In analogous procedures, the following oxime esters are prepared:

(a) Acetophenone O-[2-[p-(p-chlorophenoxy)-phenoxy]propionyl]-oxime, $n_D^{20}$: 1.5921, from p-(p-chlorophenoxy)phenol and 2-bromo-propionyl-acetophenone oxime;

(b) 2-Butanone O-[2-[p-(p-chlorophenoxy)-phenoxy]-propionyl]-oxime, $n_D^{20}$: 1.5510, from p-(p-chlorophenoxy)phenol and 2-bromo-propionyl-2-butanone oxime;

(c) 2-Butanone O-[2-[p-(p-trifluoromethylphenoxy)-phenoxy]propionyl]-oxime, $n_D^{20}$: 1.5169, from p-(p-trifluoromethylphenoxy)phenol and 2-bromo-propionyl-2-butanone oxime;

(d) Acetone O-[2-[p-(p-trifluoromethylphenoxy)-phenoxy]propionyl]-oxime, $n_D^{20}$: 1.5212, from p-(p-trifluoromethylphenoxy)phenol and 2-bromo-propionyl-acetone oxime;

(e) Acetophenone O-[2-[p-(p-trifluoromethylphenoxy)-phenoxy]propionyl]-oxime, m.p.: 102°–103°, from p-(p-trifluoromethylphenoxy)phenol and 2-bromo-propionylacetophenone oxime;

(f) 3,3,5-Trimethyl-2-cyclohexenone O-[2-[p-(p-trifluoromethylphenoxy)-phenoxy]propionyl]-oxime, $n_D^{20}$: 1.5335, from p-(p-trifluoromethylphenoxy)phenol and 2-bromopropionyl-3,5,5-trimethyl-2-cyclohexenone oxime;

(g) Cyclohexanone O-[2-[p-(p-trifluoromethyl-phenoxy)phenoxy]propionyl]-oxime, $n_D^{20}$: 1.5251, from p-(p-trifluoromethylphenoxy)phenol and 2-bromopropionyl-cyclohexanone oxime and (h) 6-Undecanone O-[2-[p-(p-trifluoromethylphenoxy)-phenoxy]propionyl]-oxime, $n_D^{20}$: 1.4999, from p-(p-trifluoromethylphenoxy)phenol and 2-bromo-propionyl-6-undecanone oxime.

The following oxime reactants for these oximes esters are prepared as described above:

2-Bromopropionyl-2-butanone oxime, $n_D^{20}$: 1.4840, from 2-butanone oxime and 2-bromopropionyl bromide;

2-Bromopropionyl-acetophenone oxime, $n_D^{20}$: 1.5650, from acetophenone oxime and 2-bromopropionyl bromide;

2-Bromopropionyl-3,5,5-trimethyl-2-cyclohexenone oxime, $n_D^{20}$: 1.5291, from 3,5,5-trimethyl-2-cyclohexenone oxime and 2-bromopropionyl bromide;

2-Bromopropionylcyclohexanone oxime, $n_D^{20}$: 1.5146, from cyclohexanone oxime and 2-bromopropionyl bromide, and 2-Bromopropionyl-6-undecanone oxime, $n_D^{20}$: 1.4760, from 6-undecanone oxime and 2-bromopropionyl bromide.

3-Butin-2-one oxime is prepared by dissolving 2.5 g of 3-butin-2-one in 10 ml of ethanol. This solution is added dropwise to a solution of 5.1 g of hydroxylamine hydrochloride and 1.6 g of sodium hydroxide in 30 ml of water at 20°. The mixture is stirred at room temperature for 2 hours, poured onto 150 ml of water and extracted with methylene chloride. The extract is washed with water, dried over sodium sulphate and evaporated. The product, 3-butin-2-one oxime is purified by adsorption onto silica gel, $n_D^{20}$: 1.424.

EXAMPLE 2

20 g of D-2-[p-(p-chlorophenoxy)phenoxy]propionic acid are stirred with 8.7 g of oxalyl chloride and 100 ml of benzene at 40° C. for 3 hours. The benzene is then distilled off in vacuo. 5 g of acetone oxime, 5.0 g of pyridine and 50 ml of tetrahydrofuran are added to the acid chloride and the mixture is stirred at room temperature for 2 hours. The reaction product is poured into water and extracted with ether. The ether extract is washed with water, dried over sodium sulphate and evaporated under reduced pressure. The product, acetone O-D-[2-[p-(p-chlorophenoxy)phenoxy]propionyl]-oxime is purified by adsorption onto silica gel, $n_D^{20}$: 1.5583.

Following analogous procedures, the following oxime esters are prepared:

(a) Acetone O-D-[2-[p-(p-trifluoromethylphenoxy)-phenoxy]propionyl]-oxime, $[\alpha]_D^{20}+50.8°$ (CHCL$_3$, 1%), from D-2-[p-(p-trifluoromethylphenoxy)phenoxy]propionic acid and acetone oxime;

(b) 2,6-Dichlorobenzaldehyde O-[2-[p-(p-trifluoromethylphenoxy)phenoxy]propionyl]-oxime, $n_D^{20}$: 1.5679, from 2-[p-(p-trifluoromethylphenoxy)phenoxy]propionic acid and 2,6-dichlorobenzaldehyde oxime;

(c) Benzaldehyde O-[2-[p-(p-trifluoromethylphenoxy)phenoxy]propionyl]-oxime, m.p. 102°–103°, from 2-[p-(p-trifluoromethylphenoxy)phenoxy]propionic acid and benzaldehyde oxime;

(d) Acetophenone O-D-[2-[p-(p-trifluoromethylphenoxy)phenoxy]propionyl]-oxime, m.p. 56°–57°, from D-2-[p-(p-trifluoromethylphenoxy)phenoxy]propionic acid and acetophenone oxime;

(e) Benzaldehyde O-2-[p-(p-chlorophenoxy)-phenoxy]propionyl-oxime, m.p. 116°–117°, from 2-[p-(p-chlorophenoxy)phenoxy]propionic acid and benzaldehyde oxime;

(f) Heptan-4-one O-2-[p-(p-trifluoromethylphenoxy)-phenoxy]propionyl-oxime, $n_D^{20}$: 1.5101, from 2[p-(trifluoromethylphenoxy)phenoxy]propionic acid and heptan-4-one oxime;

(g) 2-Methylbutan-3-one O-2-[p-(p-trifluoromethylphenoxy)phenoxy]propionyl oxime, $n_D^{20}$: 1.5105, from 2-[p-(p-trifluoromethylphenoxy)phenoxy]propionic acid and isopropyl methyl ketoxime;

(h) 4-Methyl-3-penten-2-one O-2-[p-(p-trifluoromethylphenoxy)phenoxy]propionyl oxime, $n_D^{20}$: 1.5295, from 2-[p-(p-trifluoromethylphenoxy)phenoxy]propionic acid and 4-methyl-3-penten-2-one oxime;

(i) 6-Methyl-5-hepten-2-one O-2-[p-(p-chlorophenoxy)phenoxy]propionyl oxime, $n_D^{20}$: 1.5527, from 2-[p-(p-chlorophenoxy)phenoxy]propionic acid and 6-methyl-5-hepten-2-one oxime;

(j) Cyclohexanone O-2-[p-(p-chlorophenoxy)phenoxy]propionyl oxime, $n_D^{20}$: 1.5658, from 2-[p-(p-chlorophenoxy)phenoxy]propionic acid and cyclohexanone oxime;

(k) Acetone O-2-[p-(p-bromophenoxy)phenoxy]-propionyl oxime, $n_D^{20}$: 1.5610, from 2-[p-(p-bromophenoxy)phenoxy]propionic acid and acetone oxime and (l) 3-Butin-2-one O-[2-[p-(p-trifluoromethylphenoxy)phenoxy]propionyl oxime, $n_D^{20}$: 1.5480, from 2-[p-(p-trifluoromethylphenoxy)phenoxy]propionic acid and 3-butin-2-one oxime.

EXAMPLE 3

4 g of 2-[p-(p-trifluoromethylphenoxy)phenoxy]-propionyl chloride are added dropwise to a solution of 0.8 g of acetone oxime and 1 ml of pyridine in 20 ml of tetrahydrofuran. The mixture is stirred at room temperature for 3 hours, poured onto ice and extracted with ether. The ether extract is washed with water, dried over sodium sulfate and evaporated under reduced pressure. The product, acetone O-[2-[p-(p-trifluoromethylphenoxy)phenoxy]-propionyl]-oxime, is purified by adsorption onto silica gel, $n_D^{20}$: 1.5212.

EXAMPLE 4

After 15 g of 2-[p-(p-trifluoromethylphenoxy)-phenoxy]-propionic acid are suspended in 20 ml of methylene chloride, 3.5 g of acetone oxime are added at room temperature. 9.8 g of dicyclohexylcarbodiimide, in 10 ml of methylene chloride, are then added dropwise over a period of 10 minutes as the temperature increases to about 40° C. The reaction mixture is then stirred at room temperature for 2 hours and filtered. The filtrate is evaporated to dryness on a rotary evaporator to yield acetone O-[2-[p-(p-trifluoromethylphenoxy)phenoxy]propionyl]-oxime, $n_D^{20}$: 1.5212.

EXAMPLE 5

10 g of 2-[p-(p-trifluoromethylphenoxy)phenoxy]-propionic acid are refluxed for 2 hours with 10 g of thionyl chloride and 2 drops of dimethylformamide. Excess thionyl chloride is distilled off under a water aspirater vacuum. The product is 2-[p-(p-trifluoromethylphenoxy)-phenoxy]propionic acid chloride.

10.5 g of this acid chloride are dissolve in 10 ml of toluene, and a solution of 2.4 g of acetone oxime in 3.03 g of triethylamine in 20 ml of toluene is admixed. The mixture is stirred for 1 hour, rinsed twice with 50 ml portions of water, dried over sodium sulfate and concentrated to yield acetone O-[2-[p-(p-trifluoromethylphenoxy)phenoxy]propionyl]-oxime is thus obtained, $n_D^{20}$: 1.5260.

EXAMPLE 6

Thus Example illustrates the preparation of optically active starting materials.

A. Preparation of the D-2-[p-(trifluoromethylphenoxy)-phenoxy]propionic acid ethyl ester and D-2-[p-(p-chlorophenoxy)phenoxy]propionic acid ethyl ester.

50 g of p-(p-trifluoromethylphenoxy)phenol are mixed with 38.4 g of L(−)-2-(methylsulfonyloxy)propionic acid ethyl ester. 11.4 g of anhydrous soda are added and the mixture is stirred at 110° C. for 18 hours, cooled, and 300 ml of ether are added. The organic phase is extracted by washing with 2 N NaOH and water, dried over sodium sulfate and concentrated to yield D-2-[p-(p-Trifluoromethylphenoxy)phenoxy]propionic acid ethyl ester; $[\alpha]_D^{22} = +19.2°$ (CHCl$_3$; c=1.05%).

In an analogous manner,

D-2-[p-(p-chlorophenoxy)-phenoxy]propionic acid ethyl ester, $[\alpha]_D^{20} = +28.7°$ (CHCl$_3$; c=1.05%), is prepared from p-(p-chlorophenoxy)phenol and L(−)-2-(methylsulphonyloxy)propionic acid ethyl ester.

B. Preparation of the corresponding acids by ester saponification.

58 g of D-2-[p-(p-trifluoromethylphenoxy)phenoxy]-propionic acid ethyl ester are suspended in 50 ml of methanol. 17 g of KOH (in 50 ml of water) are added and the mixture is stirred at room temperature for 1½ hours. The mixture is diluted with 200 ml of water and acidified with HCl. The resulting precipitate is filtered off, washed with water and dried to yield D-2-[p-(p-trifluoromethylphenoxy)phenoxy]propionic acid, $[\alpha]_D^{22} = +12.88°$ (CHCl$_3$; c=1.1%).

In an analogous manner,

D-2-[p-(p-chlorophenoxy)phenoxy]propionic acid, $[\alpha]_D^{20} = +20.1°$ (CHCl$_3$; c=1.01%), is prepared from D-2-[p-(p-chlorophenoxy)phenoxy]propionic acid ethyl ester.

EXAMPLE 7

This Example illustrates the preparation of an emulsifiable concentrate with a compound of this invention.

The following ingredients are admixed

| Ingredient | Amount |
| --- | --- |
| Compound of the formula I | 500 g |
| Condensation products of an alkylphenol and ethylene oxide; calcium dodecylbenzenesulphonate | 100 g |
| Epoxidized soya oil with an oxirane oxygen content of ca. 6% | 25 g |
| Butylated hydroxytoluene | 10 g |
| Xylene | to 1 liter |

EXAMPLE 8

This Example illustrates the herbicidal activity of several of the active compounds of this invention.

The compounds of formula I used as the active ingredients in the formulations in Example 8–10 are listed below. For convenience, these compounds will be identified in the Examples by the corresponding letters below.

| Compound | |
| --- | --- |
| A | Acetone 0-[2-[p-(p-chlorophenoxy)phenoxy] propionyl]-oxime |
| B | Acetone 0-[2-[p-(p-bromophenoxy)phenoxy] propionyl]-oxime |
| C | Acetone 0-[2-[p-(p-trifluoromethylphenoxy) phenoxy]-propionyl]-oxime |
| D | Acetone 0-[D-2-[p-(p-trifluoromethylphenoxy) |

| Compound | |
|---|---|
| | phenoxy]-propionyl]-oxime |
| E | Acetophenone O-[D-2-[p-(p-trifluoromethylphenoxy)-propionyl]-oxime phenoxy]-propionyl]-oxime |
| F | Cyclohexanone O-[2-[p-(p-trifluoromethylphenoxy)-phenoxy]-propionyl]-oxime |
| G | 2-Butanone O-[2-[p-(p-trifluoromethylphenoxy)-phenoxy]-propionyl]-oxime |
| H | D-2-[p-(p-trifluoromethylphenoxy)phenoxy]-propionic acid methyl ester. |

Sufficient active ingredient is dissolved in acetone to form a 2% solution. When insoluble active ingredients are used, they are formulated as wettable powders which contain kaolin as the inert diluent.

Prior to spraying, the solutions are diluted with water to a concentration sufficient to provide, on spraying application, from 156 to 1250 g of active ingredient (a.i.) per hectare.

The compounds were evaluated on *Alopecurus myosuroides, Digitaria floridana* and *Avena fatua*.

The test plants were sprayed in a greenhouse where a 16 hour day was simulated by use of mercury vapor lamps. The plants were evaluated for percent necrosis three weeks after spraying. Necrosis is a measurement of the amount of damage to a plant. 100% necrosis corresponds to complete destruction of the plant. The results are tabulated below.

| Active Ingredient | Dosage, g a.i./ha | *Alopecurus myosurcides* | % Necrosis *Digitaria floridana* | *Avena fatua* |
|---|---|---|---|---|
| A | 625 | 80 | 60 | — |
| B | 625 | 100 | 40 | — |
| C | 625 | 100 | 100 | 100 |
| C | 156 | 50 | 100 | 20 |
| D | 625 | 100 | 100 | 100 |
| D | 156 | 100 | 100 | 100 |
| E | 625 | 100 | 100 | 70 |
| F | 625 | 70 | 100 | 50 |
| G | 625 | 100 | 100 | 70 |

Solvent effects, where present, were compensated for by use of the "Abbott formula". The "Abbott formula" is described in Journal Econom. Entomology 18, 265-267 (1925).

EXAMPLE 9

This Example illustrates the effect of active compounds of this invention on *Bromus secalinus*.

The following formulations, each containing an active ingredient to be tested, were prepared by admixing the following ingredients.

| Ingredient | Amount |
|---|---|
| Active compound | 250 g/l |
| NMP | 300 g/l |
| Tensiofix B 7425 | 100 g/l |
| Phenylsulfonate CA | 25 g/l |
| Shellsol AB | to 1 liter |

NMP is 1-methyl-2-pyrrolidinone 0.08% of a wetting agent (Nonoxynyl) was added to each formulation prior to spraying.

The *Bromus secalinus* tests plants; at the 6 to 9 leaf stage, were sprayed in a greenhouse at a rate of 1000 liters/hectares.

Three weeks after spraying, the plants were evaluated for percent necrosis. Results are tabulated below.

| Active Ingredient | Dosage, g a.i./ha | % Necrosis |
|---|---|---|
| C | 0.15 | 0 |
| C | 0.31 | 0 |
| D | 0.15 | 80 |
| D | 0.31 | 90 |

EXAMPLE 10

This Example illustrates the effect of active compounds of this invention on cotton cv.Stoneville 7A.

Formulations, each containing an active ingredient to be tested, were prepared by admixing the following ingredients.

| Ingredient | Amount |
|---|---|
| Active compound | 250 g/l |
| NMP | 300 g/l |
| Tensiofix B 7425 | 100 g/l |
| Phenyl sulfonate CA | 25 g/l |
| Shellsol AB | to 1 liter |

0.08% of a wetting agent (Nonoxynol) was added to each formulation prior to spraying.

Cotton test plants, at the 2 leaf stage, were sprayed in a greenhouse at a rate of 1000 l/ha.

Ten days after spraying, the plants were evaulated for percent necrosis. Results are tabulated below.

| Active Ingredient | Dosage, g a.i./ha | % Necrosis |
|---|---|---|
| C | 1.25 | 18 |
| C | 2.5 | 50 |
| D | 1.25 | 0 |
| D | 2.5 | 28 |
| H | 1.25 | 22 |
| H | 2.5 | 48 |

EXAMPLE 11

This Example illustrates the effect of active compounds of this invention on soy beans cv. Hood.

Formulations, each containing an active ingredient to be tested, were prepared by admixing the following ingredients.

| Ingredient | Amount |
|---|---|
| Active Compound | 250 g/l |
| NMP | 300 g/l |
| Tensiofix B 7425 | 100 g/l |
| Phenysulfonate CA | 25 g/l |
| Shellsol AB | to 1 liter |

0.08% of a wetting agent (Nonoxynyl) was added to each formulation prior to spraying.

Soy bean plants, at the 2 trifoliate leaves stage, were sprayed in a greenhouse at a rate of 1000 l/ha.

Two weeks after treatment the plants were evaluated for percent necrosis. Results are tabulated below.

| Active Ingredient | Dosage, g a.i./ha. | % Necrosis |
|---|---|---|
| C | 1.25 | 10 |
| C | 2.5 | 25 |
| D | 1.25 | 0 |
| D | 2.5 | 0 |

I claim:

1. A compound of the formula

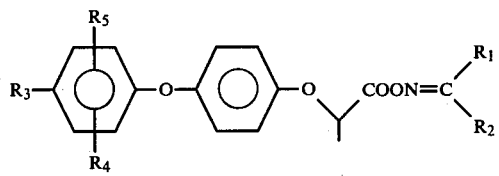

wherein $R_1$ is hydrogen, alkyl of from 1 to 6 carbons, or phenyl, $R_2$ is hydrogen, alkyl of from 1 to 6 carbons, alkenyl of from 2 to 6 carbons, alkynyl of from 2 to 6 carbons or phenyl, or $R_1$ and $R_2$, together form a cyclohexane ring, which can be mono- or dissubstituted with alkyl of from 1 to 3 carbons, $R_3$ is hydrogen, fluorine, chlorine, bromine, trifluoromethyl or nitro and $R_4$ and $R_5$ are hydrogen or chlorine, with the proviso that $R_1$ and $R_2$ are not both hydrogen;
and optical and geometric isomers thereof.

2. A compound of claim 1 wherein $R_1$ and $R_2$ are each an alkyl of from 1 to 2 carbons or phenyl, $R_3$ is chlorine or trifluoromethyl, and $R_4$ and $R_5$ are hydrogen.

3. A compound of claim 1 wherein $R_1$ and $R_2$ are each methyl, $R_3$ is chlorine or trifluoromethyl and $R_4$ and $R_5$ are hydrogen.

4. A compound of claim 1, acetone O-[2-[p-(p-chlorophenoxy)phenoxy]-propionyl]-oxime.

5. A compound of claim 1, acetone O-D-[2-[p-(p-chlorophenoxy)phenoxy]-propionyl]-oxime.

6. A compound of claim 1, acetone O-[2-[p-(p-trifluoromethylphenoxy)phenoxy]-propionyl]-oxime.

7. A compound of claim 1, acetone O-D-[2-[p-(p-trifluoromethylphenoxy)phenoxy]propionyl]-oxime.

8. A compound of claim 1, acetone O-[2-[p-(p-bromophenoxy)phenoxy]propionyl]-oxime.

9. A herbicidal composition which comprises inert carrier material and, as the active ingredient, an amount of one or more of the compounds of claim 1 which is effective as a herbicide.

10. The herbicidal composition of claim 9 wherein the active ingredient is acetone O-[2-[p-(p-chlorophenoxy)phenoxy]propionyl]-oxime.

11. The herbicidal composition of claim 9 wherein the active ingredient is acetone O-D-[2-[p-(p-chlorophenoxy)phenoxy]propionyl]-oxime.

12. The herbicidal composition of claim 9 wherein the active ingredient is acetone O-D-[2-[p-(p-trifluoromethylphenoxy)phenoxy]propionyl]-oxime.

13. The herbicidal composition of claim 9 wherein the active ingredient is acetone O-[2-[p-(p-trifluoromethylphenoxy)phenoxy]propionyl]-oxime.

14. The herbicidal composition of claim 9 wherein the active ingredient is acetone O-[2-[p-(p-bromophenoxy)phenoxy]propionyl]-oxime.

15. A method for combatting weeds which comprises applying, to the locus to be protected, a herbicidally effective amount of the compositions of claim 9.

16. A method for combatting weeds which comprises applying, to the locus to be protected, a herbicidally effective amount of the composition of claim 10.

17. A method for combatting weeds which comprises applying, to the locus to be protected, a herbicidally effective amount of the composition of claim 11.

18. A method for combatting weeds which comprises applying, to the locus to be protected, a herbicidally effective amount of the composition of claim 12.

19. A method for combatting weeds which comprises applying, to the locus to be protected, a herbicidally effective amount of the composition of claim 13.

20. A method for combatting weeds which comprises applying, to the locus to be protected, a herbicidally effective amount of the composition of claim 14.

* * * * *